(12) United States Patent
Hammerschmidt et al.

(10) Patent No.: US 7,803,617 B2
(45) Date of Patent: Sep. 28, 2010

(54) **CONDITIONAL GENE VECTORS REGULATED IN *CIS***

(75) Inventors: Wolfgang Hammerschmidt, Munich (DE); Sibille Humme, Cologne (DE); Dagmar Pich, Munich (DE); Aloys Schepers, Munich (DE)

(73) Assignee: Helmholtz Zentrum Munchen Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 457 days.

(21) Appl. No.: 11/705,952

(22) Filed: Feb. 13, 2007

(65) Prior Publication Data

US 2007/0184028 A1 Aug. 9, 2007

Related U.S. Application Data

(63) Continuation of application No. PCT/EP2005/009863, filed on Sep. 13, 2005.

(30) Foreign Application Priority Data

Sep. 14, 2004 (EP) ................... 04021854

(51) Int. Cl.
*C12N 5/10* (2006.01)
*A61K 48/00* (2006.01)

(52) U.S. Cl. .................... 435/325; 435/320.1; 435/455; 536/23.5; 536/23.72; 536/24.1

(58) Field of Classification Search ........................ None
See application file for complete search history.

(56) References Cited

U.S. PATENT DOCUMENTS

2003/0059942 A1 3/2003 Cho et al.

FOREIGN PATENT DOCUMENTS

| EP | 0826775 A | 3/1998 |
| WO | WO 00/28060 A | 5/2000 |

OTHER PUBLICATIONS

Kreppel et al. Long-term transgene expression in proliferating cells mediated by episomally maintained high-capacity adenovirus vectors. *Journal of Virology*, vol. 78, No. 1, (2004), pp. 9-22.
Krueger et al. Single-chain tet transregulators. *Nucleic Acids Research*, vol. 31, No. 12, (2003), pp. 3050-3056.
Aiyar et al., "The plasmid replicon EBV consists on multiple cis-acting elements that facilitate DNA synthesis by the cell and a viral maintenance element," The EMBO Journal. vol. 17, No. 21 pp. 6394-6403 (1998).
Baer et al., "DNA sequence and expression of the B95-8 Epstein-Barr virus genome," Nature. vol. 319 pp. 207-211 (1984).
Baron et al., "Tetracycline-controlled transcription in eukaryotes: novel transactivators with graded transactivation potential," Nucleic Acids Research. vol. 25, No. 14 pp. 2723-2729 (1997).
Campbell et al., "A monomeric red fluorescent protein," PNAS. vol. 99, No. 12 pp. 7877-7882 (2002).
Delecluse et al., "A first-generation packaging cell line for Epstein-Barr virus-derived vectors," PNAS. vol. 96 pp. 5188-5193 (1999).
Deuschle et al., "Tetracycline-Reversible Silencing of Eukaryotic Promoters," Molecular and Cellular Biology. vol. 15, No. 4 pp. 1907-1914 (1995).
Gossen, M., and Bujard, H., "Tight control of gene expression in mammalian cells by tetracycline-responsive promoters," PNAS. vol. 89 pp. 5547-5551 (1992).
Gossen et al., "Transcriptional Activation by Tetracyclines in Mammalian Cells," Science. vol. 268 pp. 1766-1769 (1995).
Hacein-Bey-Abina et al., "*LMO2*-Associated Clonal T Cell Proliferation in Two Patients after Gene Therapy for SCID-X1," Science. vol. 302 pp. 415-419 (2003).
Harrer et al., "Dynamic interaction of HMGA1a proteins with chromatin," Journal of Cell Science. vol. 117 pp. 3459-3471 (2004).
Hung et al., "Maintenance of Epstein-Barr virus (EBV) oriP-based episomes requires EBV-encoded nuclear antigen-1 chromosome-binding domains, which can be replaced by high-mobility group-I of histone H1," PNAS. vol. 98, No. 4 pp. 1865-1870 (2001).
International Search Report corresponding to International Application No. PCT/EP2005/009863 dated Feb. 21, 2006.
Kieff, E., and Rickinson, A.B., "Epstein-Barr Virus and Its Replication," Virology. Fourth Edition. vol. 2, Chapter 74 pp. 2511-2573, 2001.

(Continued)

*Primary Examiner*—Eileen B O Hara
(74) *Attorney, Agent, or Firm*—Jenkins, Wilson, Taylor & Hunt, P.A.

(57) ABSTRACT

The present invention is directed to a conditional gene vector system and to a host cell, which has been transfected with such a vector system. The present invention is further directed to a combined preparation comprising the vector system of the invention and an interfering agent. Furthermore, a pharmaceutical composition and its use in the treatment of hemophilia, diabetes, rheumatoid arthritis, genetic immunodeficiency, and graft versus host disease is provided.

23 Claims, 7 Drawing Sheets

OTHER PUBLICATIONS

Figure 1:
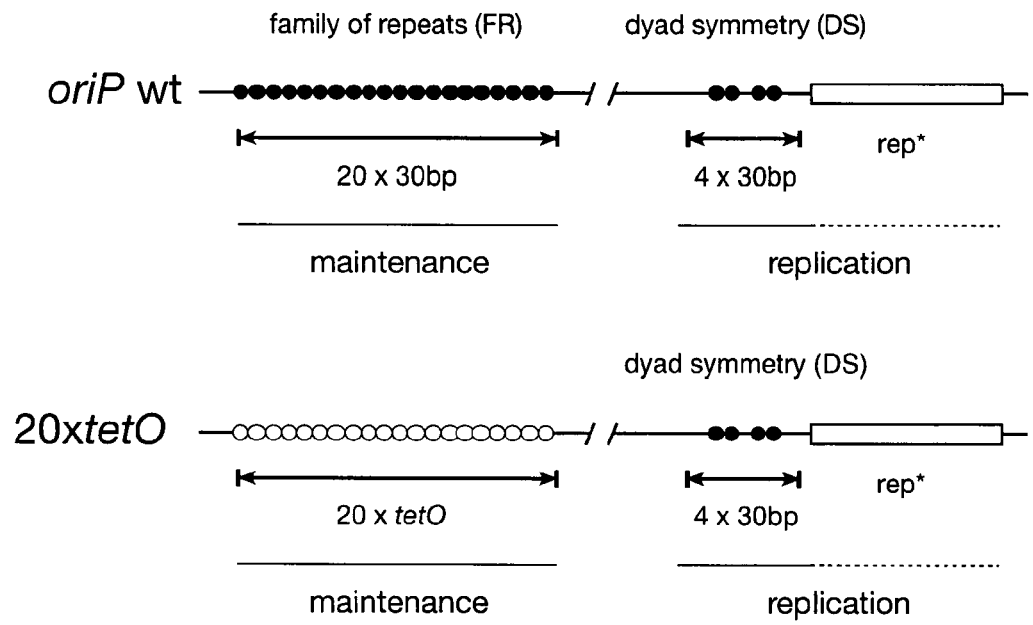

Kirchmaier and Sugden, "Plasmid Maintenance of Derivatives of *oriP* of Epstein-Barr Virus," Journal of Virology. vol. 69, No. 2 pp. 1280-1283 (1995).

Li et al., "Generation of Destabilized Green Fluorescent Protein as a Transcription Reporter," The Journal of Biological Chemistry. vol. 273, No. 52 pp. 34970-34975 (1998).

Liu et al., "Cytochemical observation of regulated bacterial β-galactosidase gene expression in mammalian cells," PNAS. vol. 86 pp. 9951-9955 (1989).

Marechal et al., "Mapping EBNA-1 Domains Involved in Binding to Metaphase Chromosomes," Journal of Virology. vol. 73, No. 5 pp. 4385-4392 (1999).

Piechaczek et al., "A vector based on the SV40 origin of replication and chromosomal S/MARs replicates episomally in CHO cells," Nucleic Acids Research. vol. 27, No. 2 pp. 426-428 (1999).

Ritzi et al., "Complex protein-DNA dynamics at the latent origin of DNA replication of Epstein-Barr virus," Journal of Cell Science. vol. 116 pp. 3971-3984 (2003).

Schaarschmidt et al., "An episomal mammalian replicon: sequence-independent binding of the origin recognition complex," The EMBO Journal. vol. 23 pp. 191-201 (2004).

Schepers et al., "Human origin recognition complex binds to the region of the latent origin of DNA replication of Epstein-Barr virus," The EMBO Journal. vol. 20, No. 16 pp. 4588-4602 (2001).

Schönig et al., "Stringent doxycycline dependent control of CRE recombinase in vivo," Nucleic Acids Research. vol. 30, No. 23 pp. 1-7 (2002).

Sears et al., "Metaphase Chromosome Tethering Is Necessary for the DNA Synthesis and Maintenance of *oriP* Plasmids but Is Insufficient for Transcription Activation by Epstein-Barr Nuclear Antigen 1," Journal of Virology. vol. 77, No. 21 pp. 11767-11780 (2003).

Sugden, B., and Leight, E.R., "EBV's Plasmid Replicon: An Enigma in *cis* and *trans*," pp. 3-11, Epstein-Barr Virus and Human Cancer, K. Takada, Editor, Jul. 2001.

Urlinger et al., "Exploring the sequence space for tetracycline-dependent transcriptional activators: Novel mutations yield expanded range and sensitivity," PNAS. vol. 97, No. 14 pp. 7963-7968 (2000).

White et al., "Infectious Delivery of 120-Kilobase Genomic DNA by an Epstein-Barr Virus Amplicon Vector," Molecular Therapy. vol. 5, No. 4 pp. 427-435 (2002).

White et al., "Sequences Adjacent to oriP Improve the Persistence of Epstein-Barr Virus-Based Episomes in B Cells," Journal of Virology. vol. 75, No. 22 pp. 11249-11252 (2001).

Yao et al., "Tetracycline Repressor, tetR, rather than the tetR-Mammalian Cell Transcription Factor Fusion Derivatives, Regulates Inducible Gene Expression in Mammalian Cells," Human Gene Therapy. vol. 9 pp. 1939-1950 (1998).

Yates, J.L., and Camiolo, S.M., "Dissection of DNA Replication and Enhancer Activation Functions of Epstein-Barr Virus Nuclear Antigen 1," Cancer Cells. vol. 6 pp. 197-205 (1988).

SEQUENCE LISTING

<160> NUMBER OF SEQ ID NOS: 1

<210> SEQ ID NO 1
<211> LENGTH: 19
<212> TYPE: DNA
<213> ORGANISM: Artificial sequence
<220> FEATURE:
<223> OTHER INFORMATION: Artifically synthesized tetO binding site

<400> SEQUENCE: 1
tccctatcag tgatagaga                                                19

CONDITIONAL GENE VECTORS REGULATED IN CIS

RELATED APPLICATIONS

This application is a continuation of PCT International Patent Application No. PCT/EP2005/009863, filed Sep. 13, 2005, which claims priority to European Patent Application No. 04021854.7, filed Sep. 14, 2004, the disclosures of each of which are incorporated herein by reference in their entirety.

The present invention is directed to a conditional gene vector system and to a host cell, which has been transfected with such a vector system. The present invention is further directed to a combined preparation comprising the vector system of the invention and an interfering agent. Furthermore, a pharmaceutical composition and its use in the treatment of hemophilia, diabetes, rheumatoid arthritis, genetic immunodeficiency, and graft versus host disease is provided.

Recombinant nucleic acids are the basis of gene vectors, which are employed for gene and immune therapy of various human diseases. Most gene vectors encompass viral or metazoan genetic components, which provide the necessary cis-acting elements such as promoters and enhancers to express one or more genes of therapeutic interest. In addition, certain gene vectors which are designed on virus blueprints also carry the essential regulatory signals involved in packaging of nucleic acids into viral structural components as well as replicative elements for the amplification of the viral vector genomes.

In the recipient cell, gene vectors can be transiently present, only, or maintained for a long period of time. In this respect, the genetic information is either rapidly lost through spontaneous degradation by cellular nucleases or maintained by integrating the genetic information into the chromosome of the recipient cell. Since a prolonged effect of the therapeutic genes and their products is often preferred in gene and immune therapy, gene vectors are commonly employed, which promote chromosomal integration of their genetic information. In particular, all retroviruses and adeno-associated viruses integrate as proviruses during this part of the viral life cycles to establish a latent or persistent state. Similarly, DNA-based gene vectors can also integrate chromosomally.

Integration of foreign DNA disrupts the genetic integrity of the host chromosome. As a result integrating viruses, viral vectors, and DNA-based gene vectors can act as insertional mutagens. Insertional mutagenesis is critically viewed since retroviral vectors, which have been used to cure a severe form of immunodeficiency in humans resulted in oncogenic T-cell transformation (Hacein-Bey-Abina et al., 2003). This problem is avoided with gene vector systems, which are maintained as extrachromosomal units in the transduced or DNA-transfected recipient cell. All gene vectors, which are characterized by this feature, are derived from recombinant DNA plasmids, which carry autonomous replicons (Piechaczek et al., 1999; Schaarschmidt et al., 2004; Sugden and Leight, 2001). Replicons are genetic units, which mediate DNA replication of the gene vector DNAs often in synchrony with the replication of the host cell chromosome.

The plasmid replicon of Epstein-Barr virus (EBV) is the latent origin of DNA replication of this human herpesvirus. Plasmids containing this origin of DNA replication replicate akin to the genome of its host cell and are maintained extrachromosomally. Consequently, this plasmid replicon has been exploited as recombinant gene vectors (Sugden and Leight, 2001). The EBV plasmid replicon, termed oriP, supports efficient DNA replication in cells selected to retain it at several copies when the viral gene product EBNA1 is provided. Recombinant plasmids containing oriP are replicated once per cell cycle during S phase and are efficiently portioned to daughter cells. Only two components, oriP in cis and EBNA1 in trans, are required; the cell contributes everything else.

The replicon oriP consists of two essential elements, the family of repeats (FR) and a structure called dyad symmetry element (DS, FIG. 1). Initiation of DNA replication takes place at or near DS to which components of the cellular pre-replication complex (pre-RC) including ORC and MCM proteins are recruited (Ritzi et al., 2003; Schepers et al., 2001). It is likely that EBNA1, which binds to four low affinity binding sites within DS, contributes to the recruitment of pre-RC, perhaps in conjunction with other structural features of DS. The FR element is an array of 20 high affinity binding motifs for EBNA1 and is dedicated to function in nuclear retention of oriP. Nuclear retention of oriP plasmids is considered mandatory for long term plasmid maintenance and might also contribute to partitioning in each cell cycle. In recombinant plasmids of up to about 30 kbps in size both components, DS and FR, are essential for oriP function. In larger recombinant plasmids (or in the context of the EBV genome) DS can become dispensable (White et al., 2001) probably because pre-RC can be recruited to areas other than DS (Schepers et al., 2001). These results suggested that DS and FR are functionally distinct cis-acting elements dedicated to DNA replication and replicon maintenance, respectively, in proliferating as well as resting cells.

Figure 2:
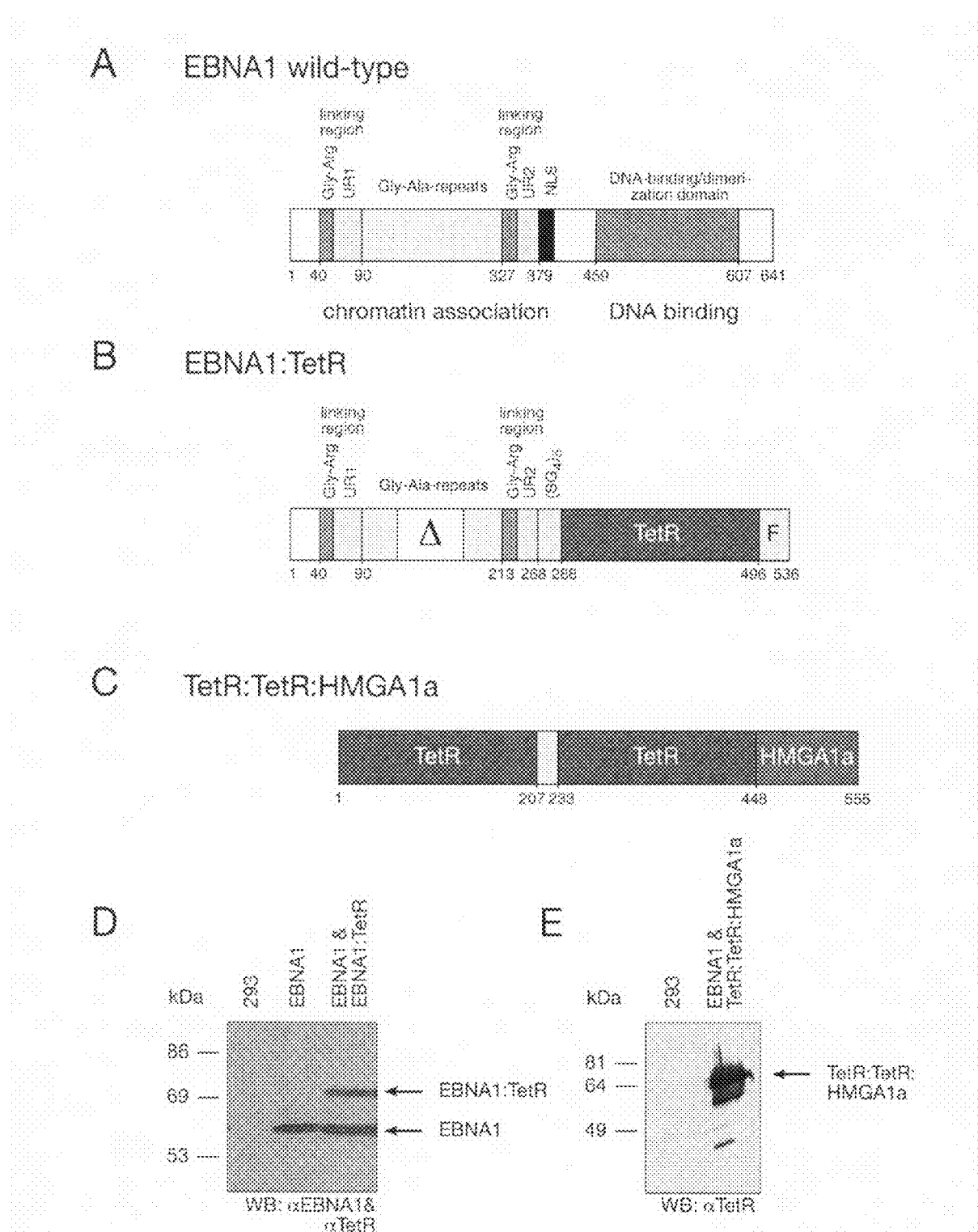

EBNA1 is a viral protein, which interacts with oriP directly and is characterized by a modular design. The carboxy-terminal half encompasses aa residues 459 to 604 of the prototype EBNA1 gene product of the B95.8 strain of EBV (Baer et al., 1984), which constitutes a dimerization and DNA-binding domain (FIG. 2). The amino-terminal half of EBNA1 in particular amino acid residues 1 to 89 and 322 to 379 mediate association with cell chromosomes (Marechal et al., 1999) and is essential for plasmid maintenance and transcriptional activation (Yates and Camiolo, 1988). The remaining domains are a glycin-alanin repeat unit (aa 90 to 327) supposedly involved in protein degradation, a nuclear localization signal (aa 379 to 386), and an acidic activation domain (aa 605 to 641)(Kieff and Rickinson, 2001 for a review).

The characteristics of chromosome association of EBNA1 triggered an approach in which its amino-terminal half was replaced with cellular proteins known to confer chromatin binding and association to mitotic chromosomes (Hung et al., 2001). Among several candidates, chimeric gene products consisting of the cellular histone H1 or HMGA1a proteins fused to amino acid residues 379 to 641 of EBNA1 functionally replaced the wild-type (wt) EBNA1 allele with respect to both plasmid replication and maintenance (Sears et al., 2003).

However, none of the references or publications teaches a system for the regulation of vector maintenance in a target cell. Such a regulation of vector maintenance could bring about the advantage to transfer genetic information into a target cell, which transfer can be easily reversed by adding an agent which is specifically adapted to remove the vector from the target cell.

Therefore, it is a problem underlying the present invention to provide a conditional gene vector system which can be advantageously used for transfecting target cells and which is capable of being removed therefrom on demand. Or, in other words, it is a problem underlying the present invention to provide gene vector systems, which can be controlled by simple means and do not alter the recipient cell(s) genetically. It is a further problem underlying the present invention to provide an improved vector system for transfecting host cells, said vector system is capable of enhancing the copy numbers of the vector. Furthermore an additional problem is to provide an improved, although reversible, binding of cis- and trans-acting elements for the above purpose.

These objects are solved by the subject-matters of the independent claims. Preferred embodiments are set forth in the dependent claims.

The solution of the present invention is the first approach to establish extrachromosomal gene vector plasmids, whose maintenance in a specific target cell can be controlled in cis by, e.g., a small molecular weight compound.

The prokaryotic tetR and lacI genes have been explored to regulate eukaryotic transcription in a conditional fashion (Gossen and Bujard, 1992; Gossen et al., 1995; Liu et al., 1989). Both gene products have been used as such (Yao et al., 1998) or fused to eukaryotic regulatory domains, which play crucial roles in transcriptional activation (VP16 and related acidic transcription activation domains)(Baron et al., 1997) or repression (KRAB)(Deuschle et al., 1995). The independent functions of the DS and FR modules of the oriP replicon, which are dedicated to DNA replication and replicon maintenance, respectively, is a recent finding (Aiyar et al., 1998; Schepers et al., 2001), which suggested that EBNA1 plays a dual role when it binds to DS and FR. The structure of EBNA1 and the FR element suggested that FR provides an array of binding moieties to which EBNA1 binds specifically and promotes the attachment of the oriP plasmids to cellular chromatin via so-called AT-hook domains (Sears et al., 2003) to ensure nuclear retention and stable plasmid maintenance. AT-hook domains are a hallmark of HMG family members (Harrer et al., 2004) of which HMGA1a binds to interphase and mitotic chromatin throughout the cell cycle. HMGA1a was also recognized to promote stable maintenance of oriP wt plasmids when fused to the DNA binding domain of EBNA1 (Hung et al., 2001).

The combinatorial approach of the present invention is illustrated herein with regard to some specific examples, i.e. to fuse the AT-hook containing regions of EBNA1 or HMGA1a to the DNA binding protein TetR. This revealed that (i) hybrid origin plasmids can be maintained extrachromosomally long-time and (ii) are lost upon doxycycline treatment, which abrogates binding of the TetR DNA binding domain.

Figure 7:
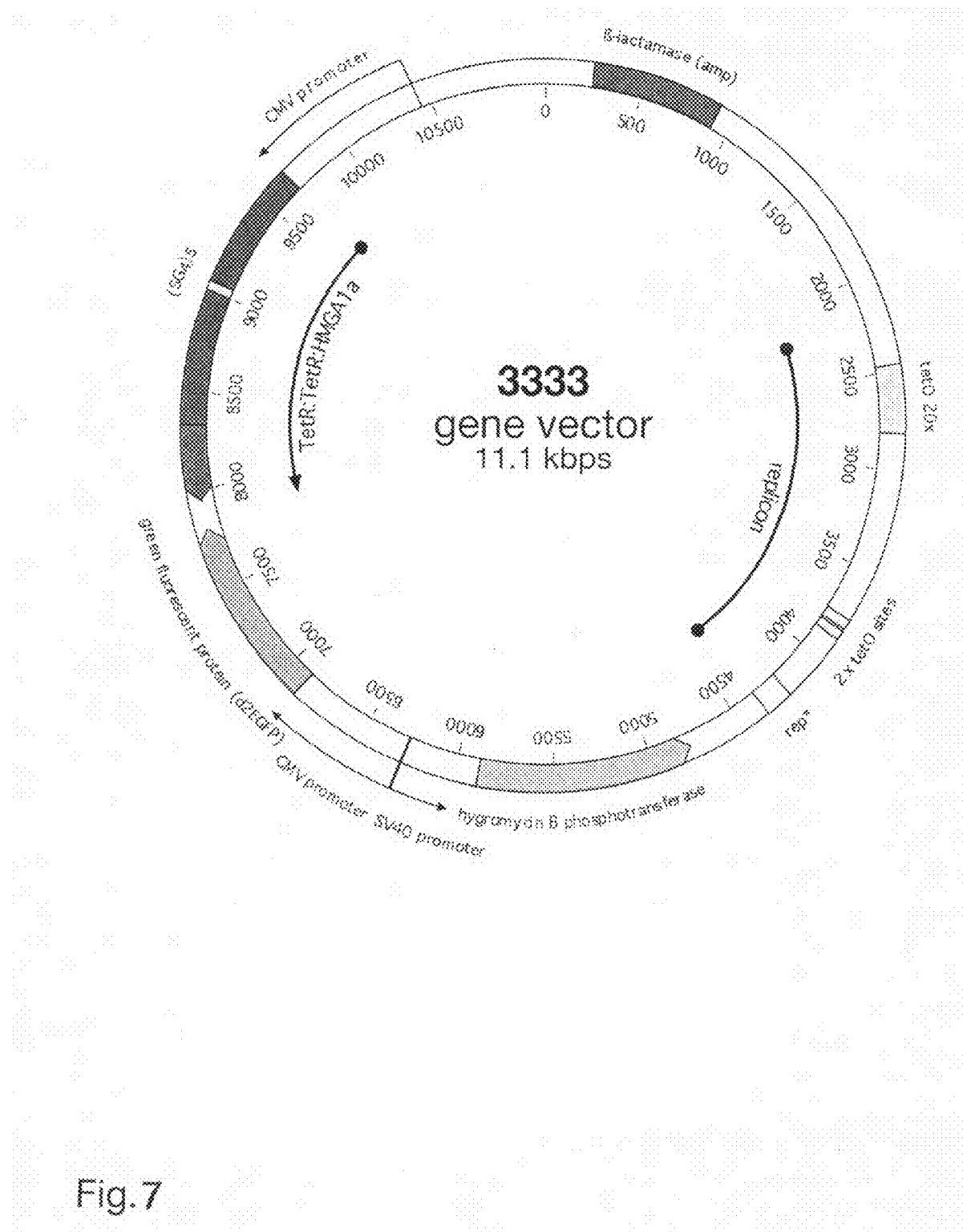

This invention further shows that synthetic, orip-like plasmid replicons can be engineered such that viral factors or domains become entirely dispensable. The four low affinity binding sites within DS (FIG. 1) can be replaced with tetO sites such that fusion proteins harboring the TetR DNA binding domain can recruit the pre-replicative complex to the origin of DNA replication as well. It was shown that such oriP-like plasmid replicons can be maintained extrachromosomally for weeks. The inventors also have evidence that doxycycline leads to a precipitous loss of such plasmids presumably because it abrogates plasmid maintenance as well as DNA replication. Such oriP-like plasmid replicons rely on fusion proteins with the TetR DNA binding domain, only, and do not require EBNA1 for their DNA replication. As a consequence, gene vector plasmids can be designed which carry the oriP-like replicon, an expression cassette encoding TetR: TetR:HMGA1a, and one or more additional genes of interest (FIG. 7 for an example).

Tetracycline-regulated gene expression has been demonstrated in vivo (Schonig et al., 2002) indicating that gene vectors, which can be regulated in cis are likely to be functionial in vivo as well. Mutants of the tetR gene with an inverse phenotype bind to tetO motifs exclusively in the presence of the drug (Gossen et al., 1995; Urlinger et al., 2000) and are expected to be functional in the present system, too. It is assumed that TetR fusions with the inverse phenotype will allow the establishment of oriP-like plasmids only in the presence of tetracycline or its derivatives, which is an even more stringent condition for plasmid gene vectors regulated in cis.

The inventors developed a first generation of gene vector plasmids, which can be regulated in cis. These gene vector plasmids carry two marker genes for selection (puromycin or hygromycin resistance) and phenotypic tracing (GFP or mRFP) which can be easily replaced with genes of therapeutic interest. Such gene vector plasmids can be packaged into a viral particle when the necessary packaging signals are provided (Delecluse et al., 1999; Kreppel and Kochanek, 2004). Additional genes or even genetic loci of therapeutic interest can be added since the packaging capacity of DNA-based plasmid vectors or viral vectors can be large, exceeding 100 kbps (White et al., 2002).

Figure 6:
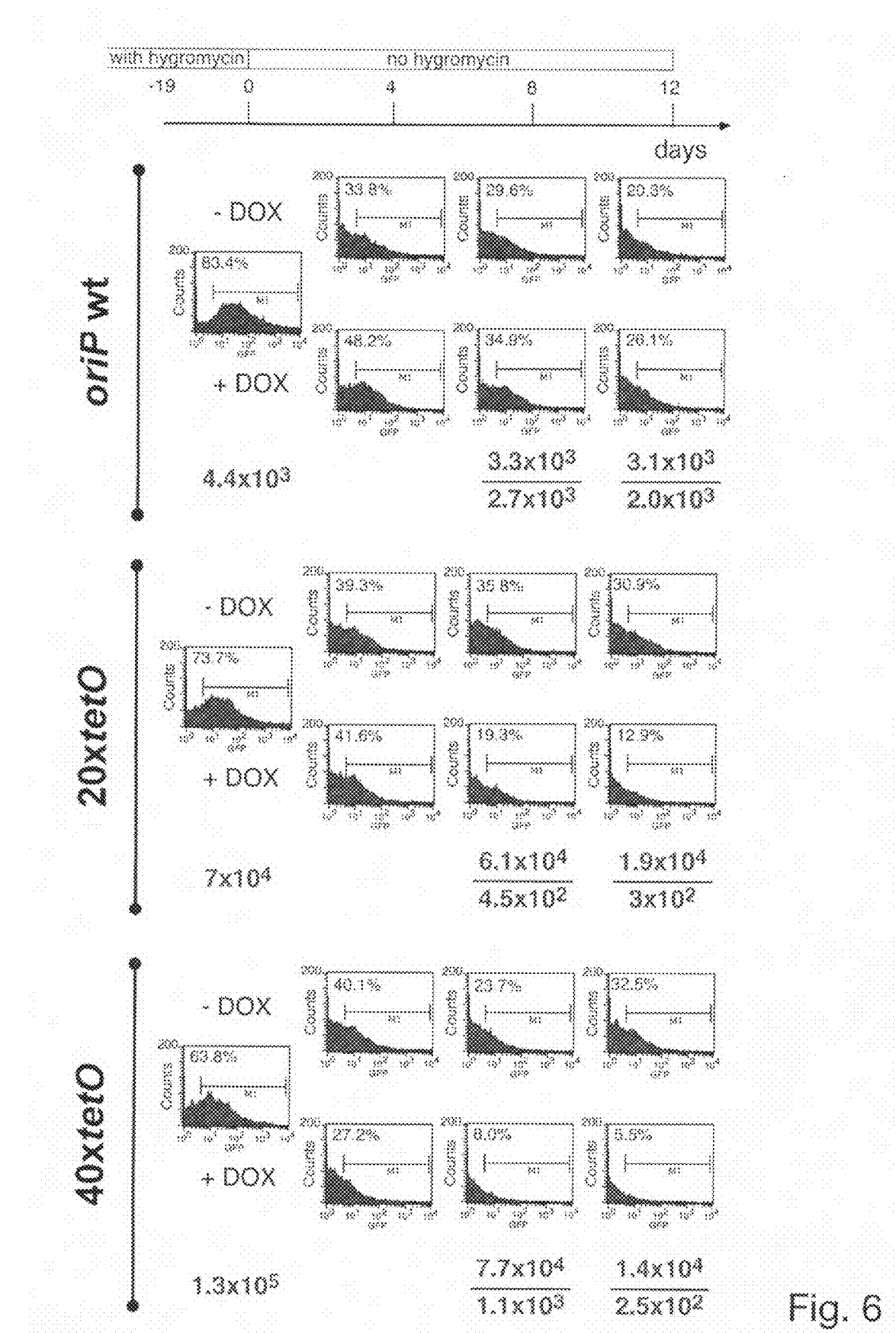

Somatic gene and immune therapy are in need of gene vector systems, which can be controlled by simple means and do not alter the recipient cell(s) genetically. The novel gene vector system presented herein offers both advantages and should contribute to the feasibility of innovative therapeutic approaches. Furthermore, the present system is providing the advantage of resulting in higher plasmid copy numbers as illustrated in FIG. 6.

The present invention is in particular directed to the following aspects and embodiments:

According to a first aspect, the present invention provides a conditional gene vector system comprising the following elements:
    a) a vector carrying a cis-acting element and one or more coding and/or non-coding sequences, and
    b) a trans-acting factor having a DNA binding domain capable of binding to a region of the cis-acting element and a domain capable of maintaining the protein in the nucleus of a target cell, characterized in that
    wherein the region of the cis-acting element and the DNA binding domain of the trans-acting factor capable of binding to the region of the cis-acting element are so selected that the nuclear maintenance of said vector carrying the cis-acting element in a target cell may be regulated by adding an agent capable of interfering with the binding of said trans-acting factor to said cis-acting element.

The term "maintenance" as disclosed herein refers to an important effect of this invention, i.e. the effect of keeping a vector in a desired target cell as long as this is wanted, for example, in an attempt of treating an animal or a human by gene therapy. "Maintenance" as used herein has a very specific meaning which should be clearly distinguished from related terms currently used in the field of science: by "maintenance" it is meant that an element, in the specific context of the present invention a trans-acting factor, is firmly attached to the nucleus of a target cell, in particular to the chromatin scaffold of the nucleus. "Firmly attached" as used herein means that the respective element is kept in the cell during all stages of the cell cycle (G1, S, and G2 stages of the cell cycle), in particular including mitosis.

The term "maintenance", therefore, can also be defined as binding capability to mitotic chromatin. It is noted that the above term has to be strictly distinguished from other characteristics, which are, for example, shown by nuclear localization sequences (NLS). Many proteins, for example transcription factors and structural nuclear proteins, must move from the cytosol into the interior of the nucleus. They are targeted to the nucleus by their nuclear localization sequence.

These proteins are actively transported through pores in the nuclear envelope into the interior. However, these NLS may only be regarded as being a transport signal and do not provide "maintenance" as explained herein, i.e. a firm (and reversible) attachment of the proteins to components of the nucleus of the target cell. Therefore, the effect of the vector system of the present invention can also be termed "plasmid maintenance and/or nuclear retention".

The terms "cis-acting element" and "trans-acting factor" as used herein have the meaning as it is commonly used in the field of science. Cis-acting elements are usually defined as DNA sequences in the vicinity of the structural portion of a gene or otherwise as a genetic unit that are functionally required. Trans-acting factors are factors, usually considered to be proteins, that bind to the cis-acting sequences to control gene expression, for example.

Someone having ordinary skill in the art may easily determine, which protein domains are capable of maintaining the protein in the nucleus of a target cell or not. This can, for example, be determined by isolating and identifying proteins that firmly attach to interface or mitotic chromatin of a cell throughout the cell cycle.

An example for a trans-acting factor in the scope of definitions set forth herein is wt EBNA1 mentioned above and discussed below, which is also illustrated in FIG. 2A. Therein, it is the wild-type EBNA1 gene product of the prototype EBV strain B95.8 with designated functional domains and their amino acid residues shown. Thus, EBNA1 has a DNA binding domain capable of binding to a region of the cis-acting element, which, in this case, is the FR sequence of oriP. Accordingly, oriP is the corresponding cis-acting element here. EBNA1, furthermore, shows a domain capable of maintaining the protein in the nucleus of a target cell termed "chromatin association" in FIG. 2A.

However, it is explicitely noted that the EBV derived EBNA1-oriP system does not show the principle of the present invention, since the nuclear maintenance of a vector carrying the oriP cis-acting element in a target cell may not be regulated by adding an agent, in particular a small molecular weight compound, capable of interfering with the binding of EBNA1 to oriP. Thus the oriP-EBNA1 system does not work in the meaning of the present invention, however, may be modified as explained below in order to solve the problems posed herein.

The term "small molecular weight compounds" as used herein is to be understood as a group of compounds having a molecular weight of between 50 and 2000, preferably 100-1000.

According to an embodiment, the cis-acting element used in the invention is derived from a naturally occurring cis-acting element, wherein the region provided for binding said cis-acting element to the corresponding naturally occurring trans-acting factor is replaced by a heterologous DNA sequence, and that the trans-acting factor is derived from a naturally occurring trans-acting factor, in which the DNA binding domain capable of binding to a region of the cis-acting element is replaced by a heterologous amino acid sequence.

For this embodiment, the above indicated modification of the oriP-EBNA1 system may serve as an example. Since the binding between oriP and EBNA1 may not be interfered or disrupted by an interfering agent, both sequences, i.e. the DNA binding domain-capable of binding to a region of the FR region of oriP are replaced by a heterologous sequence, for example by TetR, and the FR region of oriP is replaced by a tetO fragment accordingly. After this modification, a vector system will result having all elements as indicated in the first aspect of the invention, i.e. may be regulated in vivo and in vitro by a interfering agent, in this specific case by doxycycline.

Thus, the term "heterologous" sequence is not specifically limited and comprises the replacement of the naturally occurring sequences by all other sequences, whether they were derived from a related or unrelated source (in the case of EBV, it may, e.g., be derived from another virus, or as explained above, from a procaryotic source).

According to a preferred embodiment, the cis-acting element is naturally occurring and selected from the plasmid origin of DNA replication of Epstein-Barr virus, termed oriP, or from DNA motifs to which trans-acting factors bind site-specifically such as lacO operator, GAL4 binding sites, OR1/2, tetO operator, or lexA operator, which can be found in *E. coli, Saccharomyces cervisiae, phage lambda*, transposon Tn10, and *E. coli*, respectively.

As explained above, those naturally occurring cis-acting elements must be modified in order to adapt them to the regulation of an interfering agent.

According to a further embodiment, the DNA binding domain of the trans-acting factor is preferably selected from EBNA1, LacI repressor, GAL4 protein, Cro protein, the LexA protein or Tet repressor, which can be found in Epstein-Barr virus, *E. coli, Saccharomyces cervisiae, phage lambda*, transposon Tn10, *E. coli*, or humans, respectively.

Furthermore, the domain capable of maintaining the trans-acting factor in the nucleus of a target cell is preferably selected from EBNA1, Histone H1 or HMGA1a.

According to a preferred embodiment the binding region of the cis-acting element contains one or more tetO (tet operator), lacO (lac operator) sites or other operator sites derived from cis-acting elements not present in the target cell of the gene vector. This restriction must be considered in order to avoid an inappropriate site specific binding of the trans-acting factor of the invention in the target cell (leading to a binding competition with the vector carrying the cis-acting element of the invention).

In particular, tetO turned out to be preferred in the present invention, since its binding to TetR may be disrupted in the presence of doxycycline as an interfering agent.

Thus, the vector system of the invention preferably comprises a binding region of the cis-acting element which consists of at least 5×tetO to 200×tetO, preferably 10×tetO to 100×tetO, more preferably 20 to 40×tetO sites or at least 5×lacO to 200×lacO, preferably 10×lacO to 100×lacO, preferably 20 to 40×lacO sites.

The DNA binding domain of the trans-acting factor preferably is TetR (Tet Repressor) or LacI (Lac Repressor) if used in connection with the above referenced binding regions of the cis-acting elements.

Thus, in accordance with a particularly preferred embodiment of the invention, the trans-acting factor is derived from EBNA1, in which the carboxy-terminal sequences were replaced by TetR or LacI. Precisely, but merely as a preferred example than a restriction, the carboxy-terminal sequences may be defined as amino acids 379-641, more preferably 459-604 as depicted in FIG. 2A. Thus, the trans-acting factor preferably takes the form EBNA1:TetR (see FIG. 2B).

Even more preferred, in the vector system of the present invention, the trans-acting factor is HMGA1 or histone H1 fused to TetR or LacI, for example TetR:TetR:HMGA1a.

Preferably, the vector carrying the cis-acting element and one or more coding and/or non-coding sequences, and used in the present vector system is a plasmid.

The coding sequence carried in the vector is preferably selected from the group consisting of antigens, selectable and phenotypic marker proteins and genes complementing a somatic genetic defect in the target cell(s) of the gene vector. Somatic genetic defects in these genes (and diseases) and genes complementing same may be selected from the following: hemoglobin alpha, beta, gamma, delta (thalassemia); common gamma-chain cytokine receptor (SCID); adenosin deaminase (ADA immune deficiency); Bruton's tyrosine kinase (B-cell immune deficiency); clotting factor VIII (hemophilia A); clotting factor IX (hemophilia B) and lysosomal storage disorders (Morbus Gaucher, mucopolysaccharidosis, etc.).

The vector may carry coding sequences of about 120 kb.

The vector may additionally contain further non-coding sequences, for example promoter sequences in order to control transcription of the one or more coding sequences contained therein.

All essential elements of the vector system of the invention are preferably present on one single vector. An exemplary and preferred vector of this kind is depicted in FIG. 7. It carries the cis-acting replicon and the trans-acting factor TetR:TetR:HMGA1a, which are indicated in the center of the map. Two additional marker genes coding for destabilized GFP and hygromycin B phosphotransferase are functional in metazoen cells whereas the gene β-lactamase confers ampicillin resistance in E. coli.

This is the reason, why the present invention is termed "vector system", since it may provide the two essential elements, i.e. cis-acting and trans acting element separately or combined in one single vector only.

The interfering agent as used in the present invention is selected in order to be adapted to the precise cis-trans-system used, but preferably, may be selected from doxycycline, tetracycline, isopropyl-beta-D-thiogalactopyranoside (IPTG), complexing metal ions, preferably $Zn^{2+}$, or hormones.

According to a second aspect, the invention provides a host cell, which has been transfected with a vector as defined hereinabove. The trans-acting factor is also encoded by this vector. The host cell preferably is a human or animal stem cell, preferably a hematopoietic stem cell, a T cell, or a B cell, or, for example, a human embryonic stem cell.

According to a third aspect, the invention provides a combined preparation comprising:

a) the vector system as defined above and b) the intervening agent as defined herein.

In this combined preparation, components a) and b) are intended for subsequent administration (will be further explained below).

According to a further aspect, the invention provides a pharmaceutical composition containing the vector system, a host cell or a combined preparation as disclosed herein, and a pharmaceutically acceptable carrier or diluent.

Thus, the ingredients of the present invention are preferably used in form of a pharmaceutical composition where they are mixed with suitable carriers or excipients in doses to treat or ameliorate the disease. Such a composition may also contain (in addition to the ingredient and the carrier) diluents, fillers, salts, buffers, stabilizers, solubilizers and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other agents which either enhance the activity or use in treatment. Such additional factors and/or agents may be included in the pharmaceutical composition to produce a synergistic effect or to minimize side-effects.

Techniques for formulation and administration of the compounds of the instant application may be found in "Remington's Pharmaceutical Sciences", Mack Publishing Co., Easton, Pa., latest edition. Whenever the compositions are to be used for medical purposes, they will contain a therapeutically effective dose of the respective ingredient. A therapeutically effective dose further refers to that amount of the compound/ingredient sufficient to result in amelioration of symptoms, e.g., treatment, healing, prevention or amelioration of such conditions. Intravenous administration of the pharmaceutical composition of the invention to a patient is preferred.

According to a further aspect, the invention is directed to the use of the vector system or a pharmaceutical composition for the manufacture of a medicine for the treatment of hemophilia, diabetes, rheumatoid arthritis, genetic immunodeficiency, and graft versus host disease.

The invention further pertains to a method of treating a patient including the step of administering a therapeutically effective dose of a pharmaceutical composition as disclosed herein to a patient in need of said treatment. Such a treatment method follows the following protocol:

A vector, preferably comprising all essential and further non-essential elements of the invention placed on a single vector, is transferred into a host cell, preferably a hematopoietic stem cell. The host cells and vectors contained therein are propagated in vitro and subsequently, are administered to a patient suffering from a certain disease. In the patient, the expressed trans-acting element, via its DNA binding domain, binds to the binding region of the cis-acting element on the vector, thereby attaching the vector to the nucleus of the target cell in the patient via its maintenance domain. Thus, the genetic information is neither rapidly lost through spontaneous degradation by cellular nucleases nor maintained by integrating the genetic information into the chromosome of the recipient cell. In contrast, it is reversibly maintained in the nucleus of the target cell.

In the course of the treatment, the coding sequence is expressed, therefore providing the therapeutically needed product to the patient. If the treatment is complete or if it is to be interrupted, the interfering agent is adminstered to the patient, leading to a disruption of the binding of the transacting element to the cis-acting element and, thus, releases the vector, which then is removed from the target cell by degradation of cellular nucleases.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by the accompanying drawings, in which the following is shown:

FIG. 1: Schematic overview of the oriP wild-type (wt) replicon and the hybrid replicon 20×tetO. The viral replicon oriP is shown with the two elements 'family of repeats' and 'dyad symmetry', which carry 20 and 4 EBNA1 binding sites, respectively. Each EBNA1 binding site is 30 bps in size; the so-called rep* element is auxiliary and can contribute to DNA replication of oriP plasmids under certain conditions. The modification of the hybrid replicon 20×tetO constitutes an array of twenty tetO binding sites (5'-TCCCTATCAGTGATAGAGA-3') to which the TetR protein binds with high affinity.

FIG. 2: Design of trans-acting factors and cell lines. (A) Shown is the wild-type EBNA1 gene product of the prototype EBV strain B95.8 with designated functional domains and their amino acid residues. (B) The fusion gene product EBNA1:TetR with the amino-terminal domain of EBNA1 joined via an artificial linking domain [$(SG_4)_5$] to the complete coding region of the tetR gene followed by the domain F, a transcriptional activation domain derived from VP16 (Krueger et al., 2003). In contrast to wild-type EBNA1 in (A), about half of the Gly-Ala-repeats are deleted as indicated (Δ) with no functional consequences. (C) The dimeric fusion gene product TetR:TetR:HMGA1a with two tetR genes joined via the artificial linking domain as in (B). (D) Western blot analysis of the parental HEK293 cell line (left lane) and its derivatives expressing EBNA1 (center lane) and EBNA1 plus EBNA1:TetR (right lane). The proteins were detected with two monoclonal antibodies directed against the carboxy-terminus of EBNA1 and TetR. (E) Western blot analysis of the parental HEK293 cell line (left lane) and its derivatives expressing TetR:TetR:HMGA1a (right lane). The protein was detected with a monoclonal antibody directed against TetR.

Figure 3:
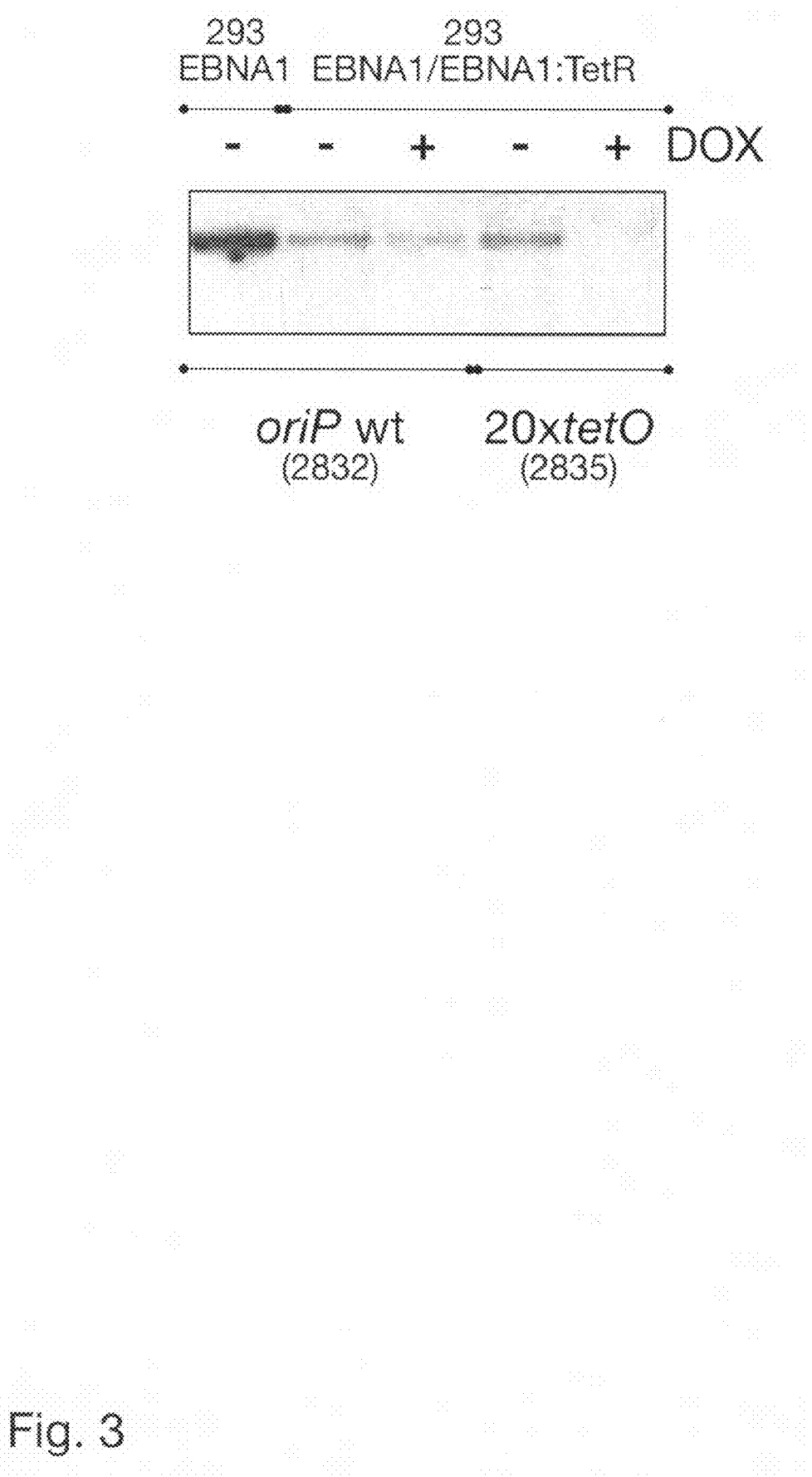

FIG. 3: TetR DNA binding domain fused to EBNA1 confers plasmid maintenance. The test plasmids 2832 (oriP wt) and 2835 (20×tetO) were separately transfected into the HEK cell line expressing both EBNA1 and EBNA1:TetR. The cells were cultivated in the presence of selective concentrations of puromycin (125 ng/ml) with or without 2.0 μg/ml doxycycline (DOX) for a few days until the cells had reached confluence. Low molecular weight DNA was isolated according to the Hirt procedure, cleaved with a restriction enzyme to linearize the test plasmids and DpnI to digest unreplicated plasmids, which retain the dam methylation pattern that the plasmids had acquired during propagation in *E. coli*. Full-length DpnI-resistant plasmid DNA was detected by Southern blot analysis with a radioactive probe, which hybridizes to the prokaryotic plasmid backbone of the test plasmids 2832 and 2835, only. Whereas doxycycline had almost no effect on the oriP wt plasmid 2832, no signal was detectable when the cells were transfected with the hybrid 20×tetO test plasmid 2835 and kept in media containing doxycycline and the selective drug puromycin. The left lane shows the oriP wt plasmid 2832 in the HEK293 cell line expressing only EBNA1. The stronger signal indicates a higher copy number of this plasmid when EBNA1 is expressed exclusively.

Figure 4:
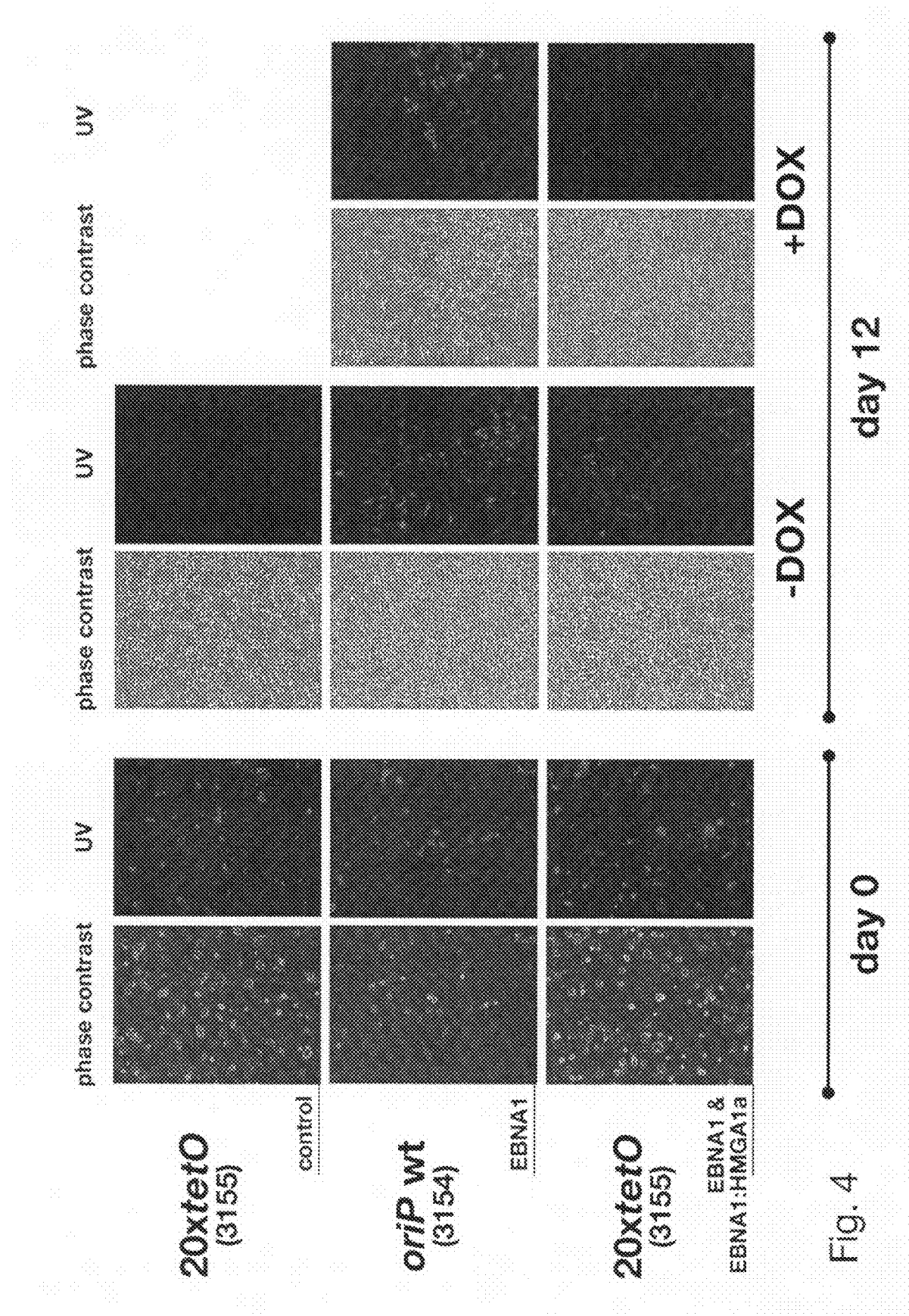

FIG. 4: Doxycycline interferes with short-term plasmid maintenance period. Three different HEK293 cell lines, which express no viral protein (control, top row panels), EBNA1 (middle row panels), and both EBNA1 plus EBNA1:TetR (bottom row panels) were used in this experiment. Two different test plasmids were examined which encode red fluorescence protein (mRFP). The plasmid 3154 carries wild-type oriP whereas 3155 is a test plasmid with the hybrid origin and 20 tetO sites (Tab. 1). The three cell lines were transfected with the test plasmids and selected with puromycin for two to four days, only, until most of the adherent cells appeared bright red under UV light in the microscope (day 0). The selective pressure was alleviated and the cells were kept in normal cell culture media with or without doxycycline (2.0 μg/ml) for a period of 12 days. No or only very few cells appeared to express mRFP in parental HEK293 cells transfected with the two test plasmids at that time point (top row and data not shown) indicating that both test plasmids were rapidly lost in the absence of EBNA1 and EBNA1:TetR. In HEK293 cells expressing EBNA1 and transfected with the oriP wt test plasmid 3154, a considerable fraction of cells still expressed mRFP in the presence or absence of doxycycline (middle row, +/− DOX) after 12 days. HEK293 cells expressing both trans-factors and transfected with the hybrid replicon test plasmid 3155 were mRFP positive, only, when the cells had been cultivated in the absence of doxycycline (bottom row).

Figure 5:
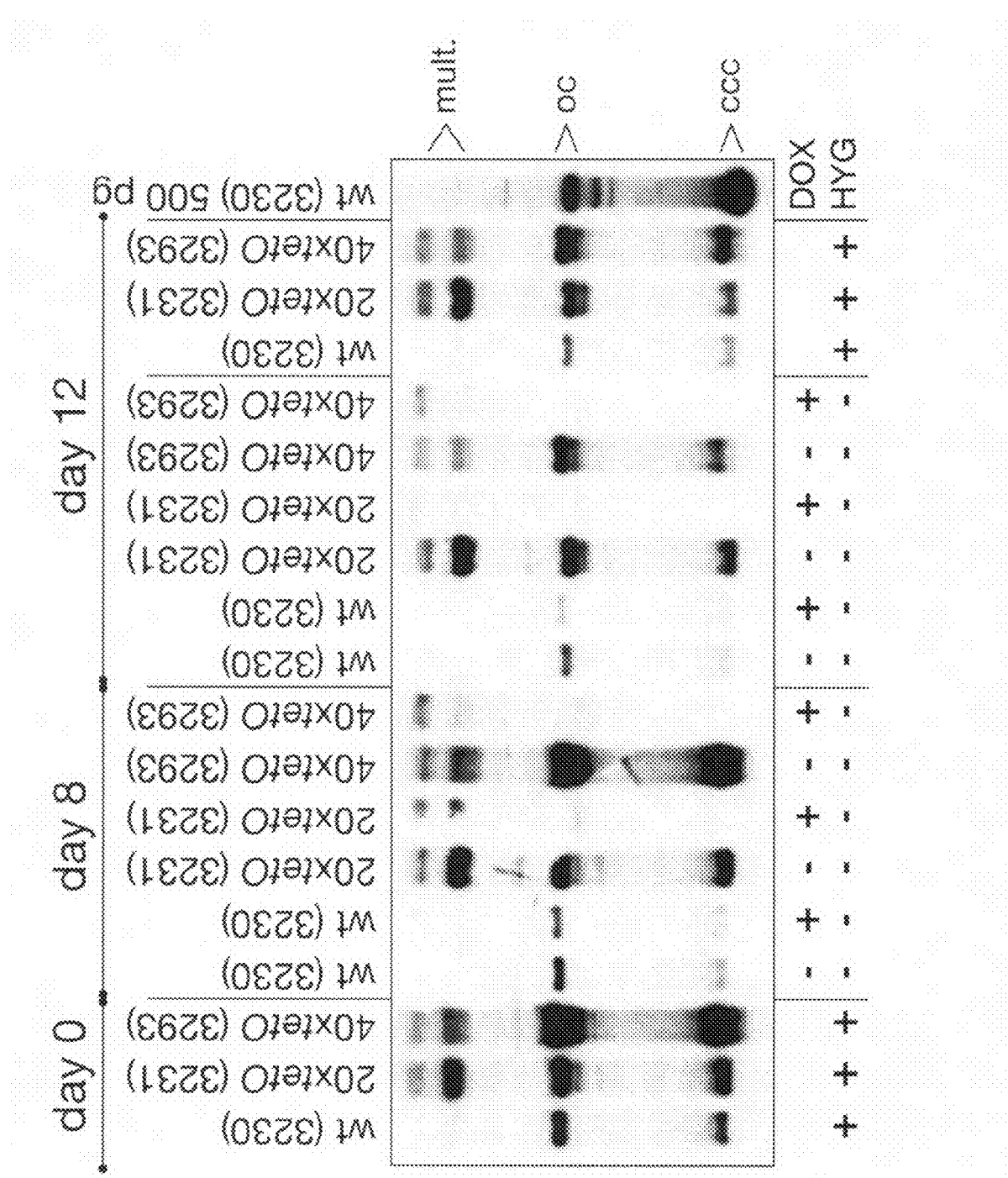

FIG. 5: Hybrid origin plasmids are precipitously lost in the presence of doxycycline. The oriP wt (3230) plasmid and the two hybrid origin plasmids 20×tetO (3231) and 40×tetO (3293) were transfected into HEK293 cells expressing both EBNA1 and TetR:TetR:HMGA1a (FIG. 2E) and selected with hygromycin (80 μg/ml) for 19 days. At that time point (day 0) selection was removed and the cells were further cultivated with or without doxycycline (DOX, 2.5 μg/ml) for 12 days. Low molecular weight DNA was prepared according to the Hirt procedure at days 8 and 12. Hirt-extracted DNAs were also prepared from the same cells, which were kept under continuous selection with hygromycin. The DNAs were cleaved with DpnI to digest traces of unreplicated plasmid DNAs and a restriction enzyme (PmlI) that cleaves cellular DNA, only, and analyzed after electrophoresis on an agarose gel by Southern blot hybridization with a radioactive probe, which hybridizes to the prokaryotic backbone of the gene vector plasmids. The control lane indicates the migration pattern of 500 pg DNA of *E. coli*-derived control plasmid 3230 with the positions of the monomeric supercoiled, covalently closed, circular (ccc), monomeric open circles (oc), and multimers (mult.) forms of plasmid DNA. The ccc and oc DNA forms indicate the presence of extrachromosomal plasmids throughout the experiment. Upon addition of doxycycline, the hybrid origin plasmids 20×tetO and 40×tetO are precipitously lost on day 8 and 12 but are maintained at higher copy numbers than wt oriP with or without hygromycin selection in the absence of doxycycline.

FIG. 6: Doxycycline downregulates vector-encoded GFP expression levels and causes the loss of plasmid copy numbers in plasmid rescue experiments. The oriP wt (3230) plasmid and the two hybrid origin plasmids 20×tetO (3231) and 40×tetO (3293) were transfected into HEK293 cells expressing both EBNA1 and TetR:TetR:HMGA1a and treated as described in FIG. 5. At days 4, 8, and 12 after omission of hygromycin from the cell culture media, the cells were analyzed by FACS for the expression of GFP encoded by all three plasmids. At days 8 and 12, Hirt-extracted DNAs were prepared and cleaved with DpnI as described in FIG. 5. 600 ng DNA of each sample was transformed via electroporation into competent DH10B *E. coli* cells. After phenotypic expression, different fractions of the *E. coli* cultures were plated on LB plates containing ampicillin (100 μg/ml) and incubated at 30° C. for 20 hours. Colonies were counted and the total number of ampicillin-resistant cells were calculated in these plasmid rescue experiments. The colony number are provided for each of the three test plasmids with or without doxycycline (DOX) as indicated.

FIG. 7: Genetic map of the plasmid 3333. Shown is a gene vector plasmid 3333, which replicates and is maintained extrachromosomally in parental HEK293 cells. The cis-acting replicon and the trans-acting factor TetR:TetR:HMGA1a are indicated in the center of the map. Two additional marker genes coding for destabilized GFP and hygromycin B phiosphotransferase are functional in metazoen cells whereas the gene β-lactamase confers ampicillin resistance in *E. coli*.

EXAMPLES

The prokaryotic TetR DNA binding domain fused to EBNA1 confers plasmid maintenance.

The inventors wanted to test two working hypotheses: (i) can a heterologous but functionally similar domain replace EBNA1's DNA binding domain? (ii) Is it possible to identify such a suitable DNA binding domain whose binding is conditional to set up a switch controlling the maintenance of oriP plasmids? Towards these goals the inventors first constructed a synthetic DNA binding protein to mimic EBNA1's function in terms of plasmid maintenance and replaced the FR element of oriP accordingly.

As shown in FIGS. 2A and B, the DNA binding domain of EBNA1 was deleted and replaced with the entire open reading frame of the prokaryotic DNA binding protein TetR. Similar to EBNA1, the tetR gene product forms homodimers and binds to its cognate DNA motif with very high affinity. In order to replace the acidic transactivation domain of EBNA1 at its distal carboxy-terminal end the inventors used a functionally equivalent domain at the same location (domain F in FIG. 2B)(Krueger et al., 2003). This chimeric protein was called EBNA1:TetR. The EBNA1.tetR gene expressed from a heterologous promoter was stably integrated with conventional methods in the HEK293 human cell line that already expresses wild-type EBNA1 as well. As shown in FIG. 2D, this cell line expresses both proteins. In order to allow binding of EBNA1:TetR to oriP, the inventors replaced the entire array of FR involved in plasmid maintenance with an identical number of direct repeats to which TetR binds with high affinity. This test plasmid called 2835 (Tab. 1) also carries a selectable maker gene for puromycin resistance and GFP as a phenotypic marker. The parental plasmid 2832 is identical to 2835 except that it carries wild-type oriP.

The test plasmids 2832 (oriP wt) and 2835 (20×tetO) were separately transfected into the HEK cell line expressing both EBNA1 and EBNA1:TetR. The cells were cultivated in the presence of selective concentrations of puromycin (125 ng/ml) with or without 2.0 μg/ml doxycycline (DOX) for a few days until the cells had reached confluence. Low molecular weight DNA was isolated according to the Hirt procedure, cleaved with a restriction enzyme to linearize the test plasmids and DpnI to digest unreplicated plasmids, which retain the dam methylation pattern that the plasmids had acquired during propagation in *E. coli*. As shown in FIG. 3, full-length DpnI-resistant plasmid DNA was detected by Southern blot analysis with a radioactive probe, which hybridizes to the prokaryotic plasmid backbone of the test plasmids 2832 and 2835, only. Whereas doxycycline had almost no effect on the oriP wt plasmid 2832, no signal was detectable when the cells were transfected with the hybrid 20×tetO test plasmid 2835 and kept in media containing doxycycline and the selective drug puromycin. This result suggested that (i) the test plasmid 2835, which carries a hybrid replicon with a multimer of 20 tetO sites at the position of the FR array can replicate and is maintained and (ii) doxycycline, which interferes with DNA binding of TetR abrogates the maintenance of this plasmid vector.

To further analyze the factors, which contribute to stable maintenance (and replication) of the hybrid replicon, the inventors used three different cell lines, which express no viral protein (parental HEK293 cells), EBNA1, and both EBNA1 plus EBNA1:TetR. For this set of experiments, two different test plasmids were used which both encode red fluorescence protein (mRFP)(Campbell et al., 2002). The plasmid 3154 carries wild-type oriP whereas 3155 is a test plasmid with the hybrid origin and 20 tetO sites (Tab. 1). The three cell lines were transfected with the test plasmids and selected with puromycin for two to four days, only, until most of the adherent cells appeared bright red under UV light in the microscope (day 0, FIG. 4). The selective pressure was alleviated and the cells were kept in normal cell culture media with or without doxycycline (2.0 μg/ml) for a period of 12 days. No or only very few cells appeared to express mRFP in parental HEK293 cells transfected with the two test plasmids at that time point (FIG. 4 top row and data not shown) indicating that both test plasmids were rapidly lost in the absence of EBNA1 and EBNA1:TetR. In HEK293 cells expressing EBNA1 and transfected with the oriP wt test plasmid 3154, a considerable fraction of cells still expressed mRFP in the presence or absence of doxycycline (+/− DOX in FIG. 4, middle row) after 12 days. HEK293 cells expressing both trans-factors and transfected with the hybrid replicon test plasmid 3155 were mRFP positive, only, when the cells had been cultivated in the absence of doxycycline (FIG. 4, bottom row). This result confirmed that the maintenance of the hybrid origin plasmid is dependent on the function of the EBNA1:TetR protein, which does not bind to tetO motifs in the presence of doxycycline (data not shown). As a consequence, hybrid oriP replicons are precipitously lost when doxycycline is added to the cell culture media.

Long-term conditional maintenance of hybrid oriP plasmids.

The amino-terminal part in the EBNA1:TetR fusion protein is expected to associate to chromatin, which is presumably essential for plasmid maintenance. Since wild-type oriP plasmids replicate and are maintained stably in the presence of another chimeric protein, HMGA1a:EBNA1 (Hung et al., 2001), we argued that a novel chimeric protein consisting of the coding sequence of HMGA1a fused to the TetR DNA-binding gene might be functional as well. It was also apparent, that the plasmid copy number of both wild-type oriP and the 20×tetO hybrid replicon was considerably lower in cells when EBNA1 and EBNA1:TetR were co-expressed (FIG. 3) presumably because the so-called linking region (FIG. 2) located in both EBNA1 and EBNA1:TetR caused heterotypic aggregations and functional interference. Thus, it seemed plausible that a fusion protein consisting of HMGA1a and TetR would circumvent these problems. To further the efficacy of the system the inventors made use of a dimeric single-chain tetR gene (Krueger et al., 2003), which binds to tetO motifs as a single protein in contrast EBNA1:TetR, which only binds as homodimers.

An expression cassette with the HMGA1a:TetR gene was stably integrated into the parental cell line HEK293 EBNA1 (FIG. 2E). The plasmids carrying oriP wt (3230, Tab. 1), and two different hybrid replicon plasmids with 20 (20×tetO; 3231) or 40 (40×tetO; 3293) copies of the tetO motif and a destabilized version of GFP (Li et al., 1998)(Tab. 1) were individually transfected into these cells, which were put under hygromycin selection (80 μg/ml) for 19 days. At that time point (day 0) selection was removed and the cells were further cultivated with or without doxycycline (2.5 μg/ml) for 12 days. The cells were analyzed by FACS for the expression of GFP at days 0, 4, 8, and 12. Low molecular weight DNAs were isolated at three time points (days 0, 8 and 12) and analyzed by Southern blot hybridization for the presence of the prokaryotic backbone of the test plasmids. DNAs were also electroporated in *E. Coli* in a plasmid rescue experiment to quantify the amount of plasmid DNA molecules by colony formation.

At day 0 of the experiment, plasmid DNAs could be detected by Southern blot hybridization (FIG. 5) and plasmid rescue in *E. coli* (FIG. 6). The majority of the cell pools expressed GFP as expected (FIG. 6). It was immediately apparent, that both hybrid plasmids (20×tetO and 40×tetO) were maintained as extrachromosomal DNAs at higher copy numbers than oriP wt (FIG. 5 and 6), although the cells did not express higher amounts of GFP (FIG. 6). Upon removal of hygromycin selection, the GFP expression levels gradually diminished in all cell pools (FIG. 6). Concomitantly, the signal intensities in the Southern blot autoradiograms became weaker indicating spontaneous loss of plasmid DNAs as reported previously (Kirchmaier and Sugden, 1995). Very much in contrast to the observed spontaneous loss, the hybrid origin plasmids 3231 and 3293 were lost precipitously in the presence of doxycycline as revealed by Southern blot analysis (FIG. 5), colony numbers of *E. coli* rescued plasmids, and GFP expression levels (FIG. 6). Quantitation of signal strengths in Southern blot analysis (FIG. 5 and data not shown) and colony numbers (FIG. 6) indicated that plasmid loss was induced by a factor of 50 to 100 in the presence of doxycycline. Reduction of GFP expression appeared not as dramatic but a substantial loss of GFP expression could be documented (FIG. 6). Doxycycline had a neglectable effect on the oriP wt plasmid 3230 (FIG. 5 and 6). In the presence of hygromycin selection, the two hybrid plasmids as well as the oriP wt control plasmid were stably maintained for the total duration the experiment (31 days, FIG. 5 and data not shown). Again, the copy number of the oriP wt plasmid was lower than the two hybrid plasmids of which the 40×tetO hybrid plasmid consistently reached the highest copy number (FIG. 5).

TABLE 1

Overview of different gene vector plasmids

| elements plasmids[+] | replicon | selectable marker | phenotypic marker |
|---|---|---|---|
| 2832 (12.2) | oriP wt | puromycin | GFP |
| 2835 (12.0) | 20xtetO; DS | puromycin | GFP |
| 3154 (12.9) | oriP wt | puromycin | mRFP |
| 3155 (12.7) | 20xtetO; DS | puromycin | mRFP |
| 3230 (8.8) | oriP wt | hygromycin | GFP |
| 3231 (8.7) | 20xtetO; DS | hygromycin | GFP |
| 3293 (8.9) | 40xtetO; DS | hygromycin | GFP |

[+]numbers in parentheses denote the size of gene vector plasmids in kbps.

REFERENCES

Aiyar, A., Tyree, C. and Sugden, B. (1998) The plasmid replicon of EBV consists of multiple cis-acting elements that facilitate DNA synthesis by the cell and a viral maintenance element. *Embo J*, 17, 6394-6403.

Baer, R., Bankier, A. T., Biggin, M. D., Deininger, P. L., Farrell, P. J., Gibson, T. J., Hatfull, G., Hudson, G. S., Satchwell, S. C., Seguin, C., Tufnell, P. S. and Barell, B. G. (1984) DNA sequence and expression of the B95-8 Epstein-Barr virus genome. *Nature*, 310, 207-211.

Baron, U., Gossen, M. and Bujard, H. (1997) Tetracycline-controlled transcription in eukaryotes: novel transactivators with graded transactivation potential. *Nucleic Acids Res*, 25, 2723-2729.

Campbell, R. E., Tour, O., Palmer, A. E., Steinbach, P. A., Baird, G. S., Zacharias, D. A. and Tsien, R. Y. (2002) A monomeric red fluorescent protein. *Proc Natl Acad Sci U S A*, 99, 7877-7882.

Delecluse, H. J., Pich, D., Hilsendegen, T., Baum, C. and Hammerschmidt, W. (1999) A first-generation packaging cell line for Epstein-Barr virus-derived vectors. *Proc Natl Acad Sci U S A*, 96, 5188-5193.

Deuschle, U., Meyer, W. K. and Thiesen, H. J. (1995) Tetracycline-reversible silencing of eukaryotic promoters. *Mol Cell Biol*, 15, 1907-1914.

Gossen, M. and Bujard, H. (1992) Tight control of gene expression in mammalian cells by tetracycline-responsive promoters. *Proc Natl Acad Sci U S A*, 89, 5547-5551.

Gossen, M., Freundlieb, S., Bender, G., Mueller, G., Hillen, W. and Bujard, H. (1995) Transcriptional activation by tetracyclines in mammalian cells. *Science*, 268, 1766-1769.

Hacein-Bey-Abina, S., Von Kalle, C., Schmidt, M., McCormack, M. P., Wulffraat, N., Leboulch, P., Lim, A., Osborne, C. S., Pawliuk, R., Morillon, E., Sorensen, R., Forster, A., Fraser, P., Cohen, J. I., de Saint Basile, G., Alexander, I., Wintergerst, U., Frebourg, T., Aurias, A., Stoppa-Lyonnet, D., Romana, S., Radford-Weiss, I., Gross, F., Valensi, F., Delabesse, E., Macintyre, E., Sigaux, F., Soulier, J., Leiva, L. E., Wissler, M., Prinz, C., Rabbitts, T. H., Le Deist, F., Fischer, A. and Cavazzana-Calvo, M. (2003) LMO2-associated clonal T cell proliferation in two patients after gene therapy for SCID-X1. *Science*, 302, 415-419.

Harrer, M., Luhrs, H., Bustin, M., Scheer, U. and Hock, R. (2004) Dynamic interaction of HMGA1a proteins with chromatin. *J Cell Sci*, 117, 3459-3471.

Hung, S. C., Kang, M. S. and Kieff, E. (2001) Maintenance of Epstein-Barr virus (EBV) oriP-based episomes requires EBV-encoded nuclear antigen-1 chromosome-binding domains, which can be replaced by high-mobility group-I or histone H1. *Proc Natl Acad Sci U S A*, 98, 1865-1870.

Kieff, E. and Rickinson, A. B. (2001) Epstein-Barr virus and its replication. In Knipe, D. M., Howley, P. M., Griffin, D. E., Martin, M. A., Lamb, R. A., Roizman, B. and Straus, S. E. (eds.), *Fields' Virology*. Lippincott-Williams & Wilkins, Philadelphia, Vol. 2, pp. 2511-2573.

Kirchmaier, A. L. and Sugden, B. (1995) Plasmid maintenance of derivatives of oriP of Epstein-Barr virus. *J. Virol.*, 69, 1280-1283.

Kreppel, F. and Kochanek, S. (2004) Long-term transgene expression in proliferating cells mediated by episomally maintained high-capacity adenovirus vectors. *J Virol*, 78, 9-22.

Krueger, C., Berens, C., Schmidt, A., Schnappinger, D. and Hillen, W. (2003) Single-chain Tet transregulators. *Nucleic Acids Res*, 31, 3050-3056.

Li, X., Zhao, X., Fang, Y., Jiang, X., Duong, T., Fan, C., Huang, C. C. and Kain, S. R. (1998) Generation of destabilized green fluorescent protein as a transcription reporter. *J Biol Chem*, 273, 34970-34975.

Liu, H. S., Feliciano, E. S. and Stambrook, P. J. (1989) Cytochemical observation of regulated bacterial beta-galactosidase gene expression in mammalian cells. *Proc Natl Acad Sci U S A*, 86, 9951-9955.

Marechal, V., Dehee, A., Chikhi-Brachet, R., Piolot, T., Coppey-Moisan, M. and Nicolas, J. C. (1999) Mapping EBNA-1 domains involved in binding to metaphase chromosomes. *J Virol*, 73, 4385-4392.

Piechaczek, C., Fetzer, C., Baiker, A., Bode, J. and Lipps, H. J. (1999) A vector based on the SV40 origin of replication and chromosomal S/MARs replicates episomally in CHO cells. *Nucleic Acids Res*, 27, 426-428.

Ritzi, M., Tillack, K., Gerhardt, J., Ott, E., Humme, S., Kremmer, E., Hammerschmidt, W. and Schepers, A. (2003) Complex protein-DNA dynamics at the latent origin of DNA replication of Epstein-Barr virus. *J Cell Sci*, 116, 3971-3984.

Schaarschmidt, D., Baltin, J., Stehle, I. M., Lipps, H. J. and Knippers, R. (2004) An episomal mammalian replicon: sequence-independent binding of the origin recognition complex. *Embo J*, 23, 191-201.

Schepers, A., Ritzi, M., Bousset, K., Kremmer, E., Yates, J. L., Harwood, J., Diffley, J. F. and Hammerschmidt, W. (2001)

Human origin recognition complex binds to the region of the latent origin of DNA replication of Epstein-Barr virus. *Embo J*, 20, 4588-4602.

Schonig, K., Schwenk, F., Rajewsky, K. and Bujard, H. (2002) Stringent doxycycline dependent control of CRE recombinase in vivo. *Nucleic Acids Res*, 30, e134.

Sears, J., Kolman, J., Wahl, G. M. and Aiyar, A. (2003) Metaphase chromosome tethering is necessary for the DNA synthesis and maintenance of oriP plasmids but is insufficient for transcription activation by Epstein-Barr nuclear antigen 1. *J Virol*, 77, 11767-11780.

Sugden, B. and Leight, E. R. (2001) EBV's plasmid replicon: an enigma in cis and trans. *Curr Top Microbiol Immunol*, 258, 3-11.

Urlinger, S., Baron, U., Thellmann, M., Hasan, M. T., Bujard, H. and Hillen, W. (2000) Exploring the sequence space for tetracycline-dependent transcriptional activators: Novel mutations yield expanded range and sensitivity. *Proc Natl Acad Sci U S A*, 97, 7963-7968.

White, R. E., Wade-Martins, R. and James, M. R. (2001) Sequences adjacent to oriP improve the persistence of Epstein-Barr virus-based episomes in B cells. *J Virol*, 75, 11249-11252.

White, R. E., Wade-Martins, R. and James, M. R. (2002) Infectious delivery of 120-kilobase genomic DNA by an Epstein-Barr virus amplicon vector. *Mol Ther*, 5, 427-435.

Yao, F., Svensjo, T., Winkler, T., Lu, M., Eriksson, C. and Eriksson, E. (1998) Tetracycline repressor, tetR, rather than the tetR-mammalian cell transcription factor fusion derivatives, regulates inducible gene expression in mammalian cells. *Hum Gene Ther*, 9, 1939-1950.

Yates, J. L. and Camiolo, S. M. (1988) Dissection of DNA replication and enhancer activation functions of Epstein-Barr virus nuclear antigen 1. *Cancer Cells*, 6, 197-205.

regulated by adding an agent capable of interfering with the binding of said trans-acting factor to said cis-acting element.

2. The vector system of claim 1, wherein the cis-acting element is derived from a naturally occurring cis-acting element, wherein the region provided for binding said cis-acting element to the corresponding naturally occurring trans-acting factor is replaced by a heterologous DNA sequence, and that the trans-acting factor is derived from a naturally occurring trans-acting factor, in which the DNA binding domain capable of binding to a region of the cis-acting element is replaced by a heterologous amino acid sequence.

3. The vector system of claim 2, wherein the cis-acting element is naturally occurring and selected from the plasmid origin of DNA replication of Epstein-Barr virus, termed oriP, or from DNA motifs to which trans-acting factors bind site-specifically.

4. The vector system of claim 1, wherein the DNA binding domain of the trans-acting factor is selected from EBNA1, Lacl repressor, GAL4 protein, Cro protein, the LexA protein or Tet repressor.

5. The vector of claim 1, wherein the domain capable of maintaining the trans-acting factor in the nucleus of a target cell is selected from EBNA1, Histone H1 or HMGA1a.

6. The vector system of claim 1, wherein the binding region of the cis-acting element contains one or more tetO (tet operator), lacO (lac operator) sites or other operator sites derived from cis-acting elements not present in the target cell of the gene vector.

7. The vector system of claim 6, wherein the binding region of the cis-acting element consists of at least 5×tetO to 200× tetO, preferably 10×tetO to 100×tetO, more preferably 20 to 40×tetO sites or at least 5×lacO to 200×lacO, preferably 10×lacO to 100×lacO, preferably 20 to 40×lacO sites.

What is claimed is:

1. A conditional gene vector system comprising the following elements:
  a) a vector carrying a cis-acting element and one or more coding and/or non-coding sequences, and
  b) a trans-acting factor having a DNA binding domain capable of binding to a region of the cis-acting element and a domain capable of maintaining the trans-acting factor in the nucleus of a target cell,
  wherein the region of the cis-acting element and the DNA binding domain of the trans-acting factor capable of binding to the region of the cis-acting element are so selected that the nuclear maintenance of said vector carrying the cis-acting element in a target cell may be 8. The vector system of claim 6 or 7, wherein the DNA binding domain of the trans-acting factor is TetR (Tet Repressor) or Lacl (Lac Repressor).

9. The vector system of claim 1, wherein the trans-acting factor is derived from EBNA1, in which the carboxy-terminal sequences were replaced by TetR or Lacl.

10. The vector system of claim 1, wherein the trans-acting factor is HMGA1 or histone H1 fused to TetR or Lacl.

11. The vector system of claim 1, wherein the vector is a plasmid.

12. The vector system of claim 1, wherein the coding sequence carried in the vector is selected from the group consisting of antigens, selectable and phenotypic marker proteins and genes complementing a somatic genetic defect in the target cell(s) of the gene vector.

13. The vector system of claim 1, wherein the interfering agent is selected from doxycyclin, tetracycline, isopropyl-beta-D-thiogalactopyranoside (IPTG), complexing metal ions, preferably $Zn^{2+}$, or hormones.

14. The vector system of claim 1, wherein all elements of said vector system are present on one single vector.

15. An isolated host cell, which has been transfected with a vector system of claim 1.

16. The isolated host cell of claim 15, which is a human or animal stem cell.

17. The host cell of claim 16, wherein the isolated human or animal stem cell is selected from the group consisting of a hematopoietic stem cell, a T cell, and a B cell.

18. A combined preparation comprising:
   a) the vector system of claim 1; and
   b) an agent capable of interfering with the binding of said trans-acting factor to said cis-acting element.

19. The combined preparation of claim 18, wherein components a) and b) are intended for subsequent administration.

20. The vector system of claim 3, wherein the DNA motifs are selected from the group consisting of lacO operator, GAL4 binding sites, OR1/2, tetO operator, and lexA operator.

21. A conditional gene vector system comprising the following elements:
   a) a vector carrying a cis-acting element and one or more coding and/or non-coding sequences, wherein the cis-acting element is a tetO-operator,
   b) a trans-acting factor having a DNA binding domain capable of binding to a region of the cis-acting element and a domain capable of maintaining the trans-acting factor in the nucleus of a target cell, wherein the DNA binding domain of the trans-acting factor is a Tet repressor,
   wherein the region of the cis-acting element and the DNA binding domain of the trans-acting factor capable of binding to the region of the cis-acting element are so selected that the nuclear maintenance of said vector carrying the cis-acting element in a target cell may be regulated by adding an agent capable of interfering with the binding of said trans-acting factor to said cis-acting element, wherein the domain capable of maintaining the trans-acting factor in the nucleus of a target cell is EBNA1.

22. The combined preparation of claim 18 wherein the interfering agent is selected from doxycyclin, tetracycline, isopropyl-beta-D-thiogalactopyranoside (IPTG), complexing metal ions, or hormones.

23. The combined preparation of claim 22 wherein the complexing metal ions comprise $Zn^{2+}$.

* * * * *